United States Patent
Peters et al.

(10) Patent No.: US 11,357,895 B2
(45) Date of Patent: Jun. 14, 2022

(54) METHOD AND APPARATUS FOR DEGASSING LIQUIDS

(71) Applicant: Fresenius Medical Care Deutschland GmbH, Bad Homburg (DE)

(72) Inventors: Arne Peters, Bad Homburg (DE); Gerome Fischer, Weberstedt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 222 days.

(21) Appl. No.: 16/762,190

(22) PCT Filed: Nov. 8, 2018

(86) PCT No.: PCT/EP2018/080605
§ 371 (c)(1),
(2) Date: May 7, 2020

(87) PCT Pub. No.: WO2019/092101
PCT Pub. Date: May 16, 2019

(65) Prior Publication Data
US 2020/0360586 A1 Nov. 19, 2020

(30) Foreign Application Priority Data
Nov. 8, 2017 (DE) ............ 10 2017 126 136.2

(51) Int. Cl.
*A61M 1/16* (2006.01)
*A61M 1/30* (2006.01)

(52) U.S. Cl.
CPC ............ *A61M 1/1658* (2013.01); *A61M 1/30* (2013.01); *A61M 2205/3382* (2013.01); *A61M 2205/3386* (2013.01)

(58) Field of Classification Search
CPC ............ A61M 1/1658; A61M 1/30; A61M 2205/3382; A61M 2205/3386; B01D 19/0063
See application file for complete search history.

(56) References Cited

U.S. PATENT DOCUMENTS 4,371,385 A 2/1983 Johnson

FOREIGN PATENT DOCUMENTS

DE 102015119237 5/2017
GB 561 366 5/1944
(Continued)

*Primary Examiner* — Dirk R Bass
(74) *Attorney, Agent, or Firm* — Jacobson Holman PLLC

(57) ABSTRACT

The present invention relates to an apparatus for degassing liquids comprising a degassing system, wherein the degassing system has a first degassing chamber, a second degassing chamber, a liquid store, a pump, and a supply line that connects the liquid store to the first degassing chamber; wherein the pump is connected to the first degassing chamber at the intake side and to the second degassing chamber at the pressure side; and wherein the degassing system furthermore has a return line that can be cut off and that connects the two degassing chambers to one another, and wherein the apparatus comprises a controller that is configured to operate the degassing system in a first operating mode and in a second operation mode; wherein the degassing system is connected in the first operation mode such that the pump conducts liquid away from the first degassing chamber and supplies it to a removal unit for degassed liquid; and wherein the degassing system is connected in the second operating mode such that liquid is returned from the second degassing chamber to the first degassing chamber through the return line.

14 Claims, 7 Drawing Sheets

(56) References Cited

FOREIGN PATENT DOCUMENTS

Figure 1:
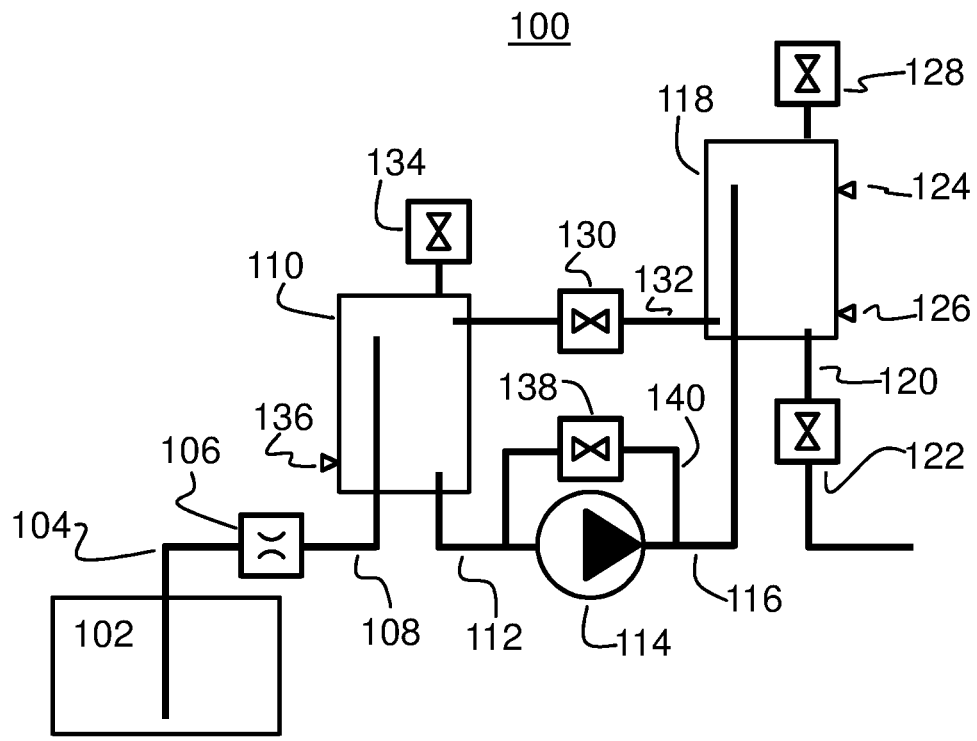

| GB | 561366 | 5/1944 |
|----|--------|--------|
| WO | WO2017/137178 | 8/2017 |

METHOD AND APPARATUS FOR DEGASSING LIQUIDS

The present invention relates to a method and to an apparatus for degassing liquids and to the use of the liquid provided in accordance with the invention.

It is known from the prior art to use liquids to prepare medical solutions and in particular dialysis solutions, wherein non-occlusive pumps such as rotary pumps or impeller pumps are frequently used for conveying these liquids. These pumps have a number of advantages. However, they suffer from the disadvantage that air bubbles can collect in the interior of the pumps, whereby the conveying power of the pumps is reduced and damage can possibly be caused to the pump, e.g. by cavitation, which reduces the service life of the pump.

It is therefore the underlying object of the present invention to provide an apparatus and a method for preparing a liquid in which apparatus/method this problem no longer occurs or only occurs to a minor extent.

This object is solved by an apparatus having the features of claim 1 and by a method having the features of claim 9.

Two air separation chambers, also called degassing chambers or chambers in the following, are preferably used, with one of the chambers preferably being located hydraulically upstream of the pump and the other preferably being located hydraulically downstream of the pump.

Each of the degassing chambers preferably has a respective valve for atmospheric pressure equalization.

The degassing chambers are connected to one another by a return line so that liquid can flow from the second degassing chamber to the first degassing chamber. This return line preferably has a cut-off means, e.g. a valve, a hose clamp or the like, by means of which it can be cut off and opened.

The apparatus for degassing liquids in accordance with the invention comprises a degassing system, wherein the degassing system has a first degassing chamber, a second degassing chamber, a liquid store, a pump, and a supply line that connects the liquid store to the first degassing chamber, wherein the pump is connected to the first degassing chamber at the intake side and to the second degassing chamber at the pressure side, and wherein the degassing system furthermore has a return line that can be cut off and that connects the two degassing chambers to one another. The apparatus furthermore has a controller such as a control and regulation unit that is configured to operate the degassing system in a first operating mode and in a second operation mode, wherein the degassing system is connected in the first operation mode such that the pump conducts liquid away from the first degassing chamber and supplies it to a removal unit for degassed liquid, and wherein the degassing system is connected in the second operating mode such that liquid is returned from the second degassing chamber to the first degassing chamber through the return line.

The first operating mode is thus characterized in that the pump, preferably a non-occlusive pump, directly or indirectly sucks in liquid that is at least partly degassed from the first degassing chamber and conveys this liquid directly or indirectly to a removal unit. This removal unit can, for example, be a distributor or a line, a container, etc. or also an apparatus by means of which a medical liquid, in particular a dialysis solution, can be prepared. The apparatus can be a dialysis machine that has means for preparing a dialysis solution from the liquid provided.

The degassing takes place in the first degassing chamber and, optionally, also already before the entry of the liquid into the first degassing chamber, that is in the supply line through which liquid flows from the liquid store into the first degassing chamber or through which the liquid is sucked by the pump. A restrictor can be arranged in the supply line for this purpose that effects a pressure drop that produces an improved degassing of the liquid.

The liquid that is prepared by the apparatus in accordance with the invention or by the method in accordance with the invention is preferably water such as RO water.

The pump can be connected directly or indirectly to the first degassing chamber at the intake side and directly or indirectly to the second degassing chamber at the pressure side. It is, for example, conceivable that in the first operating mode the pump sucks in liquid directly from the first degassing chamber at the intake side or sucks in liquid indirectly such as from the first degassing chamber via the second degassing chamber.

Provision can be made at the pressure side that the pump conveys directly to the removal unit or also indirectly, for example such that the pump first conveys into the second degassing chamber and the liquid moves from there to the removal unit.

Provision is made in a further embodiment of the invention that the controller is configured such that the pump is operated in a conveying mode in both operating modes or that the pump is only operated in a conveying mode in the first operating mode, but not in the second operating mode. "Conveying mode" is to be understood such that the pump produces a net conveyance at which liquid is conveyed to the removal unit; that is not a circuit flow in which the pump is admittedly likewise in operation, but no liquid is conveyed to the removal unit.

It is conceivable that the first and second conveying chambers are arranged relative to one another such that the liquid moves through the return line from the second degassing chamber into the first degassing chamber due to gravity in the second operating more or that this is done due to the conveying power of the pump.

In a further embodiment, the two degassing chambers can be arranged spatially separate from one another.

However, the case is also covered by the invention that they are arranged in a common construction unit that has a partition wall that separates the two degassing chambers from one another. The partition wall can be opened and closed by a valve or by another cut-off unit.

In a further embodiment of the invention, only the first degassing chamber is connected to the liquid store. In this case, there is no fluid communication between the second degassing chamber and the liquid store.

However, the case is also covered by the invention that both degassing chambers are connected or connectable to the liquid store so that depending on the operating mode preset by the controller the first or the second degassing chamber is in fluid communication with the liquid store.

To enable a largely continuous or completely continuous provision of degassed liquid to the removal unit, two degassing systems can be provided that are connected in parallel, with the controller being configured such that the degassing systems are operated alternately such that the first degassing system is operated in the first operating mode and the second degassing system is simultaneously operated in the second operating mode and vice versa. The two degassing systems can be identical or also different.

Both of the degassing chambers preferably have at least one level sensor by means of which the level in the degassing chamber can be measured or at least the exceeding or falling below of a limit value for the level can be detected.

The controller can be configured to switch over from the first to the second operating mode or from the second to the first operating mode when a level sensor fires. The controller is preferably designed such that it switches over from the first to the second operating mode when the level sensor of the first degassing chamber falls below a limit value and/or the level sensor exceeds a limit value in the second degassing chamber and/or switches over from the second to the first operating mode when the level sensor exceeds a limit value in the first degassing chamber and/or falls below a limit value in the second degassing chamber.

The present invention furthermore relates to a method having the features of claim 9.

Provision is accordingly made that liquid is withdrawn from the first degassing chamber and is provided to a removal unit for degassed liquid in the first operating mode and that liquid is conducted back from the second degassing chamber into the first degassing chamber in the second operating mode.

In this respect, in the first operating mode, liquid can be conveyed from the first degassing chamber via the second degassing chamber to a removal unit by means of the pump or liquid can be conveyed directly from the first degassing chamber (without involvement of the second degassing chamber) to a removal unit or to the second chamber.

A switchover is preferably made from the first operating mode to the second operating mode when the liquid level in the first degassing chamber falls below a limit value and/or when the liquid level exceeds a limit value in the second degassing chamber.

A switchover is preferably made from the second operating mode to the first operating mode when the liquid level in the second degassing chamber falls below a limit value and/or when the liquid level exceeds a limit value in the first degassing chamber.

It is conceivable that degassed liquid is only provided to the removal unit in the first operating mode or both in the first and in the second operating modes.

Provision is made in a further embodiment of the invention that both degassing chambers are arranged in a common construction unit that has a partition wall that separates the two degassing chambers from one another, wherein a valve or another cut-off element is provided in the partition wall that is open in the first operating mode and is closed in the second operating mode.

The present invention further relates to the use of an apparatus in accordance with any one of the claims 1 to 8 or to a method in accordance with any one of the claims 9 to 14 for preparing a medical solution, in particular for preparing a dialysis solution.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment shown in the drawing.

Figure 15:
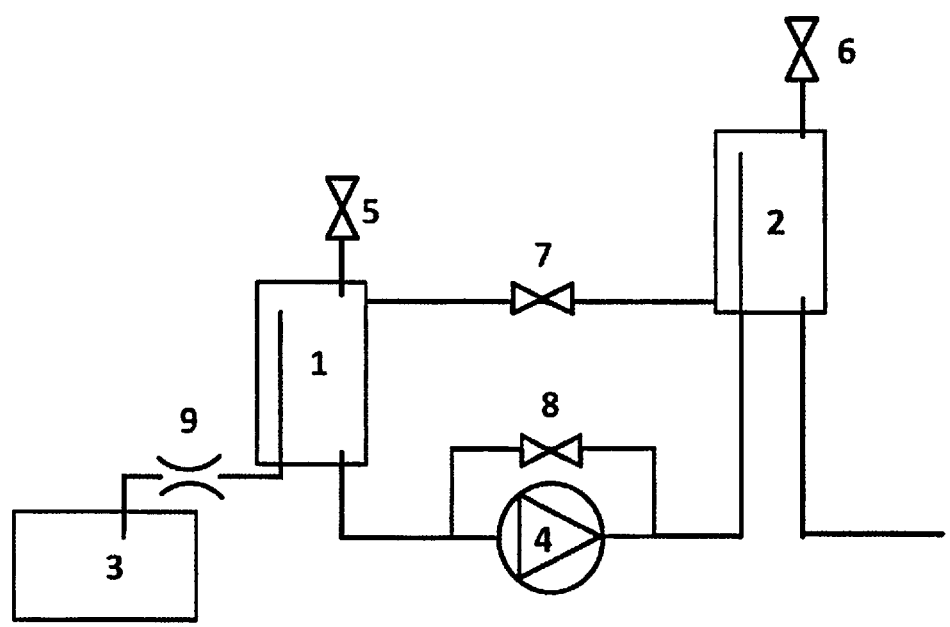

There are shown:

FIGS. 1-4: a schematic representation of the apparatus in accordance with the invention in a first embodiment in different operating modes;

FIGS. 5-8: a schematic representation of the apparatus in accordance with the invention in a second embodiment in different operating modes;

FIGS. 9-14: a schematic representation of the apparatus in accordance with the invention in a third embodiment in different operating modes; and FIG. 15: a simplified schematic representation of the apparatus in accordance with the invention.

FIG. 15 shows a simplified representation of the apparatus in accordance with the invention.

The apparatus comprises two degassing or air separation chambers 1, 2, wherein the one of the chambers is located hydraulically upstream of the pump 4 and one of the chambers is located hydraulically downstream of the pump 4.

A refill connector for topping up the storage container 3 is not shown in the Figures.

The air separation chambers will also be called degassing chambers or simply chambers in a representative manner within the framework of the present invention.

Both chambers 1, 2 each have a valve 5, 6 at the top for an atmospheric pressure equalization and are connected to one another through a return line by a valve 7 located therein. The term "valve" stands as representative for any desired cut-off member within the framework of the present invention. It can e.g. be a hose clamp, a valve or the like.

The air separation from the liquid is carried out as follows:

Liquid is degassed from the storage container 3 or via a supply line, optionally via a restrictor 9. The air/water mixture moves into the air separation chamber 1. The non-occlusive pump 4 conveys from there and conveys degassed liquid into the second air separation chamber 2. The chamber 2 can be filled by means of the pump 4 with an open air separation valve 6. The chamber 2 is located at the pressure side of the pump 4.

The conveying of the liquid from the storage container 3 into the first chamber 2 preferably takes place by means of the vacuum generated by the pump 4. This generally applies in a preferred embodiment and not only to the embodiment shown in FIG. 15.

Both chambers have means for detecting the liquid level such as ultrasound sensors, conductivity sensors, etc.

The level of the liquid in the first chamber 1 falls due to the conveying by means of the pump 4. If it falls below a specific level, both chambers are connected by means of the valve 7 and are opened to the atmosphere via the valves 5 and 6. This produces an increase in the liquid level in chamber 1 and a drop in the liquid level in chamber 2.

In this process, the pump 4 is either slowed down or completely switched off or fluidically connected with an open valve 8 by means of the connection line so that practically no conveying into chamber 2 takes place. If the chamber 1 has been sufficiently filled, the return operation is terminated by the closing of the valve 7 and by the switchover into the normal conveying operation of the pump 4. The pump 4 now again conveys liquid from the first chamber 1 into the second chamber 2.

A further valve is preferably located in the outflow line of the second chamber 2 that is shown at the far right without a reference numeral in FIG. 15 to decouple the degassing apparatus shown in FIG. 15 from the adjoining part of an apparatus such as a hydraulic unit of a dialysis machine while the above-described two-stage method (degassing operation—return operation) or at least the return operation, i.e. the second operating mode, is running.

FIG. 1 shows a more detailed embodiment for an apparatus 100 for degassing a liquid.

The apparatus comprises a first chamber 110 and a second chamber 118, wherein the chamber 110 is located hydraulically upstream of the pump 114, i.e. at the intake side of the pump 114, and the second chamber 118 is located hydraulically downstream of the pump 114, i.e. at the pressure side of the pump 114.

The pump 114 is connected to the chamber 110 by means of the line 112 at its intake side and is connected to the chamber 118 by means of the line 116 at its pressure side. A connection line 140 is furthermore provided in which a valve 138 is arranged and which connects the pressure side of the pump 114 to its intake side.

Both chambers 110, 118 each have a bleed valve 134, 128 via which the chambers 110, 118 can be opened with respect to the atmosphere and can thus be vented.

As can furthermore be seen from FIG. 1, the two chambers 110, 118 are directly connected to one another via a return line 132. The valve 130 is located in the line 132.

The chambers 110, 118 furthermore have level sensors 136 (in the first chamber 110) and 124, 126 (in the second chamber 118). The level within the chambers or the exceeding or falling below of specific level limits can be detected by means of these level sensors. The chamber 110 only has one level sensor 136, whereas the chamber 118 is equipped with two level sensors 124, 126 that are spaced apart from one another in a vertical direction.

The first chamber is connected at the inflow side to a storage container 102 via the line 104, 108 in which a restrictor 106 is located.

The second chamber 118 is connected to an outflow line 120, i.e. to a removal unit in accordance with the invention, in which a valve 122 is arranged. The degassed fluid flows through this line with an open valve 122 and is put to use and serves, for example, the preparation of a dialysis solution.

All of the valves shown can be opened or closed as required and according to a work cycle.

The pump 114 is preferably a non-occlusive pump such as a rotary pump, an impeller pump, etc.

Figure 2:
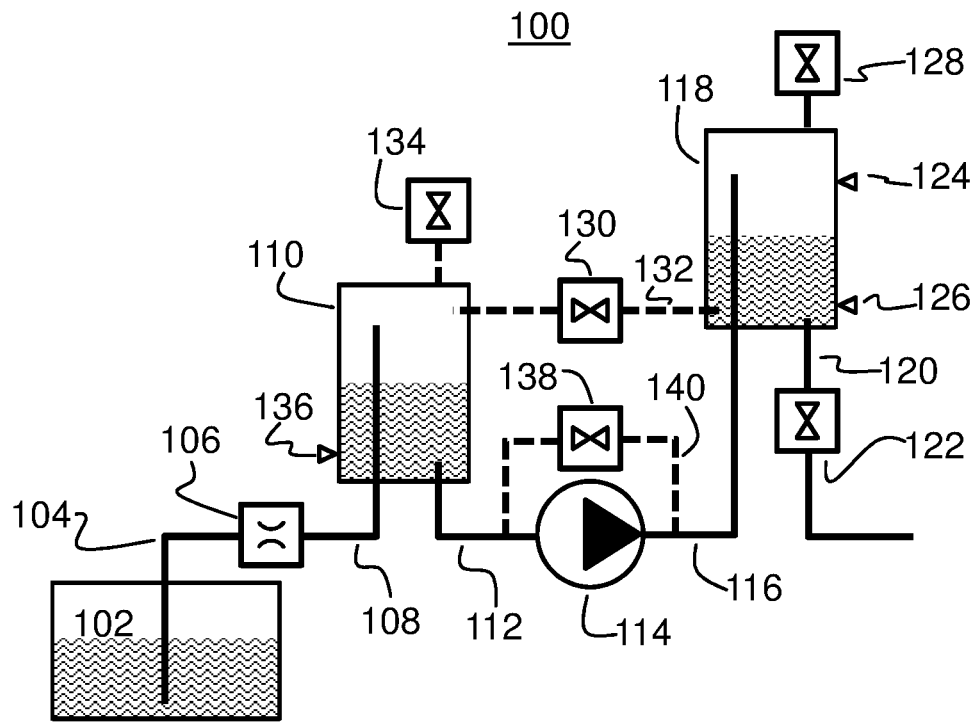
Figure 3:
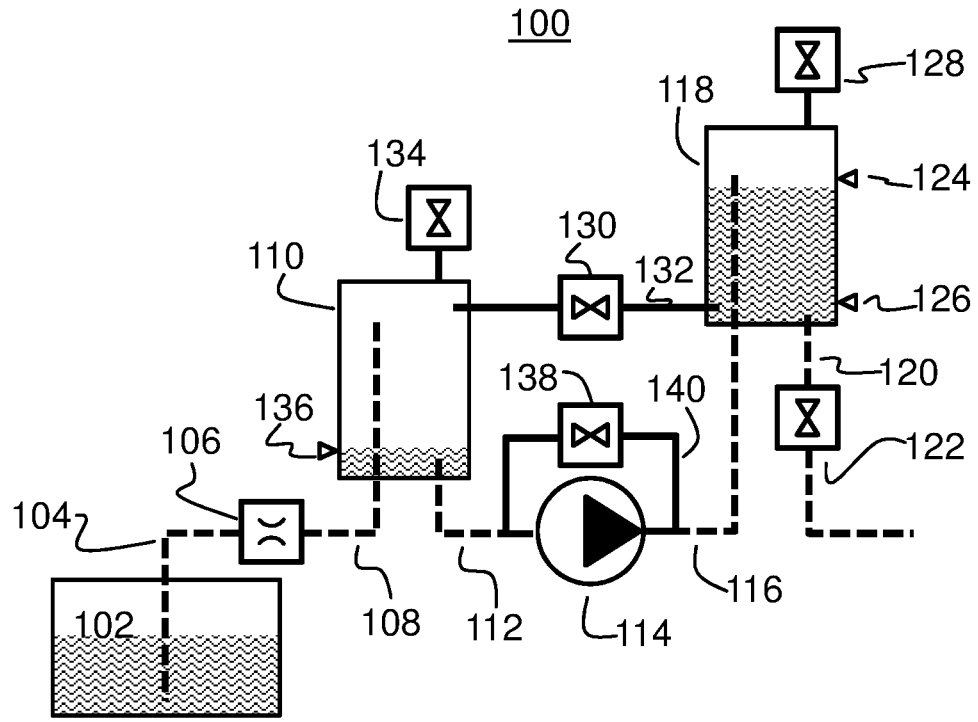

The method for air separation from the liquid is carried out as follows:

FIG. 2 shows the degassing operation and FIG. 3 shows the return operation that is subsequent to the degassing operation. The degassing thus takes place in two stages, preferably in batch operation, i.e. discontinuously.

Dashed lines in the Figures show closed lines; solid lines shown open lines.

The degassing operation in accordance with FIG. 2 is as follows:

Liquid flows from the storage container 102 through the lines 104, 106 into the first chamber 110 and is already degassed in so doing. The degassing process is assisted by means of the optionally present restrictor 106. The air/water mixture moves into the air separation chamber 110, i.e. into the first chamber whose degassing valve 134 is closed.

The valve 130 in the connection line, i.e. in the return line 132, is likewise closed. The pump 114 conveys the degassed liquid from the first chamber 110 into the air separation chamber 118, i.e. into the second chamber, whose degassing valve 128 is open with respect to the atmosphere so that the second chamber 118 is vented. This is preferably the case when liquid is actively removed from the second chamber 118 by means of a pump, not shown, or by means of gravity. If this is not the case, the valve 128 can remain closed when the pump 114 conveys into the second chamber 118 and the excess pressure then adopted in the second chamber 118 can be used to convey the liquid through the line 120.

The connection line 140 of the pump 114 is closed by closing the valve 138.

Some of the degassed liquid is supplied via the line 120 to a use such as to an apparatus for preparing a dialysis solution. The valve 122 of the line 120 is open during the degassing operation. If the degassing performance, i.e. the amount of degassed liquid in the second chamber 118, is higher than required, i.e. higher than the discharge amount through the line 120, an upper level sensor 124 can trigger an interruption of the degassing operation. Alternatively, a return of liquid from the second chamber 118 into the first chamber 110 can take place in ongoing operation, i.e. with a running pump 114; the line 132 is opened in this case. This principle is only used or only works when conveying takes place actively from the second chamber 118 by means of a pump or when gravity is sufficient for the discharge by means of the line 120 and when the supply of degassed liquid is higher than the net withdrawal from the second chamber 118.

The degassing operation in accordance with FIG. 2 is terminated when the level sensor 136 of the first chamber 110 has fired, i.e. when the level of the liquid in the first chamber 110 has dropped down to the level sensor 136.

FIG. 3 shows the then subsequent return operation, i.e. the second operating mode. The pump 114 is connected in that the line 140 is opened by opening the valve 138. There is thus no net conveyance or substantially no net conveyance from the first chamber into the second chamber. The lines 112 and 116 are thus not flowed through or are only negligibly flowed through. No liquid or substantially no liquid thus also flows in the lines 104 and 108, as is marked by the dashed line, since the pump does not generate any vacuum in the first chamber 110 that, in accordance with FIG. 2, produces an inflow of liquid from the storage container 102 into the first chamber 110.

The line 120 is closed by means of the valve 122, i.e. no withdrawal of degassed liquid to a consumer takes place. The line 132 or its valve 130 is open so that degassed liquid flows back from the second chamber into the first chamber. The bleeders 128 and 134 are open in this process.

The return from the second chamber into the first chamber takes place by gravity. The case is generally also covered by the invention that a pump is used for this purpose.

Figure 4:
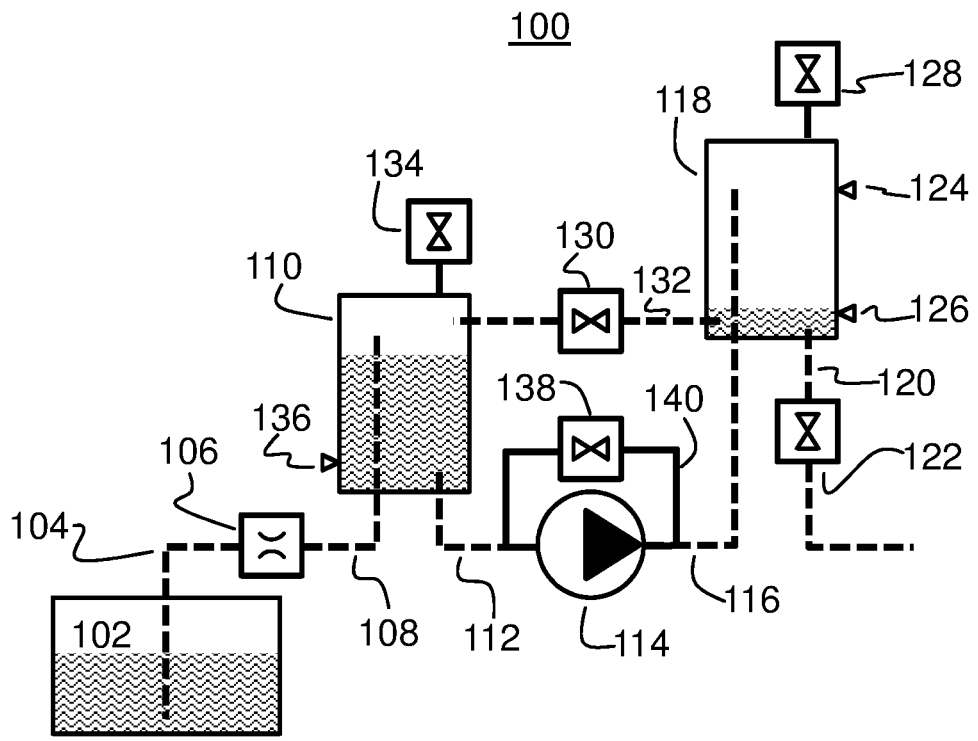

The liquid level drops in the second chamber 118 and rises in the first chamber 110 by this return. The end of the return operation is shown in FIG. 4 and is characterized in that the liquid level in the second chamber 118 reaches the lower level sensor 126.

Subsequently, all the lines and the pump 114 are again switched into degassing operation, i.e. into the first operating mode, as is shown in FIG. 2.

The apparatus in accordance with FIGS. 1-4 preferably operates discontinuously ("batch degassing"), i.e. degassed liquid is not supplied for extraction through the line 120 continuously, but only batch-wise.

However, the continuous provision of degassed liquid is also covered by the invention. Reference is made to FIGS. 5 to 8 for this purpose.

Two identical degassing systems such as were described with respect to FIGS. 1 to 4 are provided in parallel for this purpose, with the same reference numerals in FIGS. 5 to 8 designating the same or functionally the same parts as in FIGS. 1 to 4 and with the parts of the one degassing system (called "degassing system a" in the following) being marked by the additional letter a and the parts of the other degassing system (called "degassing system b" in the following) being marked by the additional letter b. The total system is designated by 200.

Figure 5:
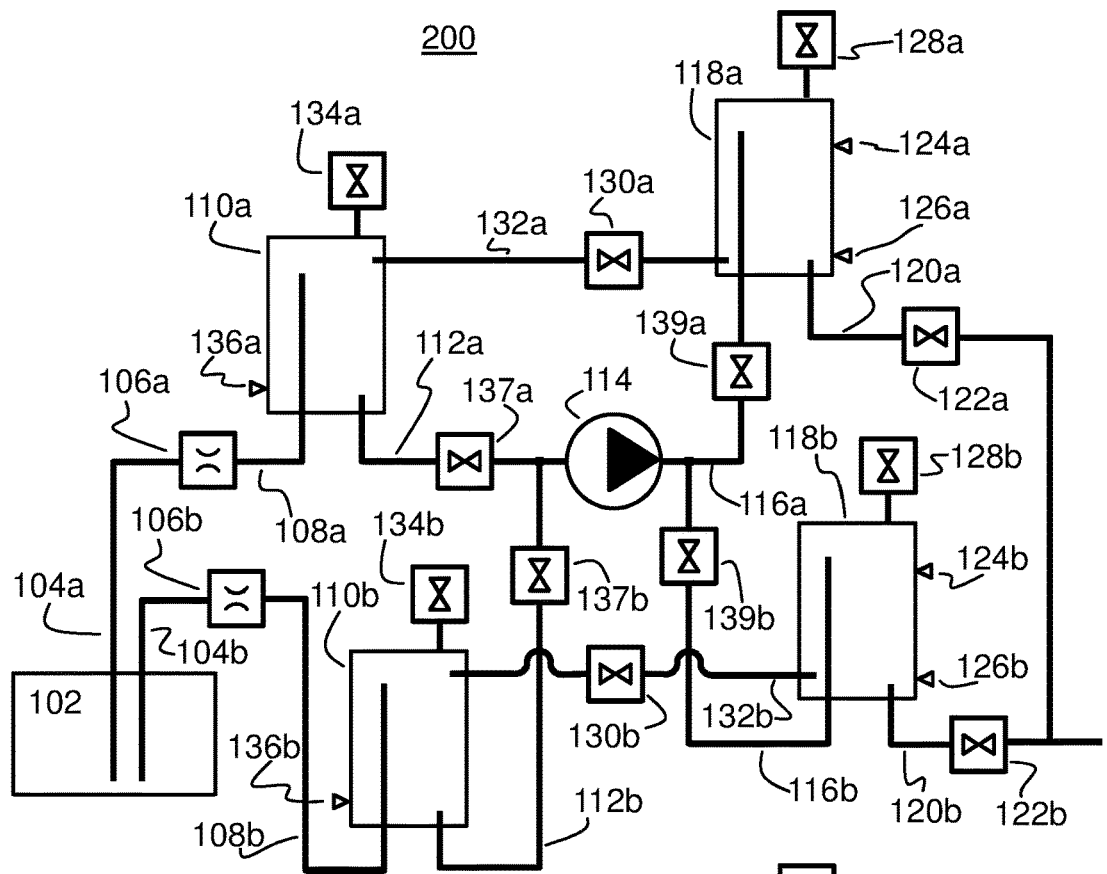

As can be seen from FIG. 5, both first chambers 110a and 110b are respectively connected to the same storage container 102 and obtain the liquid to be degassed from it. The outflow lines of the two second chambers 118a and 118b furthermore open into the same outflow line in which the degassed liquid is provided for further use.

The valves 137a and 137b that are each arranged between the first chambers 110a and 110b and the common pump 114 and the valves 139a and 139b that are each arranged between the common pump 114 and the second chambers 118a and 118b serve for the switching over between both degassing systems a and b.

The two degassing systems a and b are operated alternately, i.e. if the degassing takes place in one degassing system (first operating mode), the return takes place in the other system (second operating mode) and vice versa so that degassed liquid can always be withdrawn for further use in the line with alternatively open valves 122a or 122b.

Figure 6:
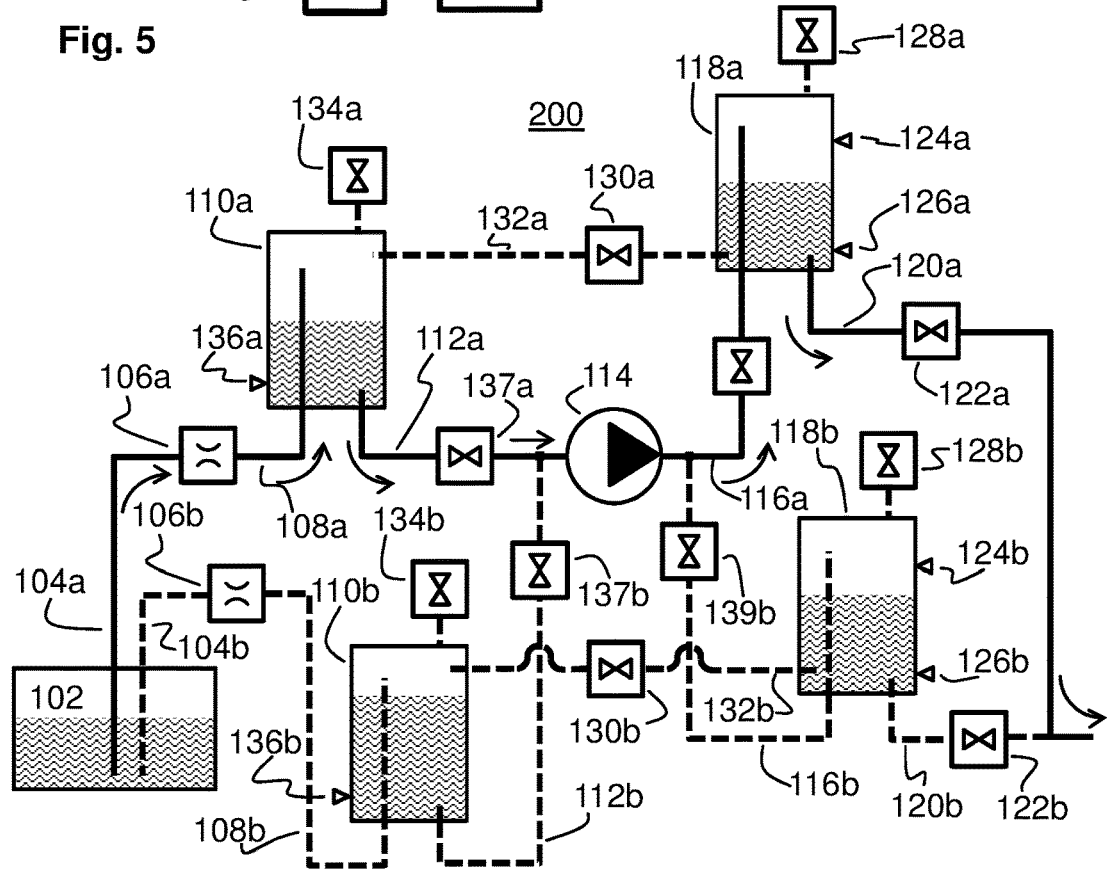

FIG. 6 shows the state in which the degassing takes place in degassing system a and degassed liquid is provided via the line 120a with an open valve 122a. The pump 114 for this purposes conveys liquid from the first chamber 110a into the second chamber 118a with an open valve 137a and a closed valve 137b. All the valves in degassing system b are closed so that neither a degassing nor a return from the second chamber into the first chamber takes place there.

Figure 7:
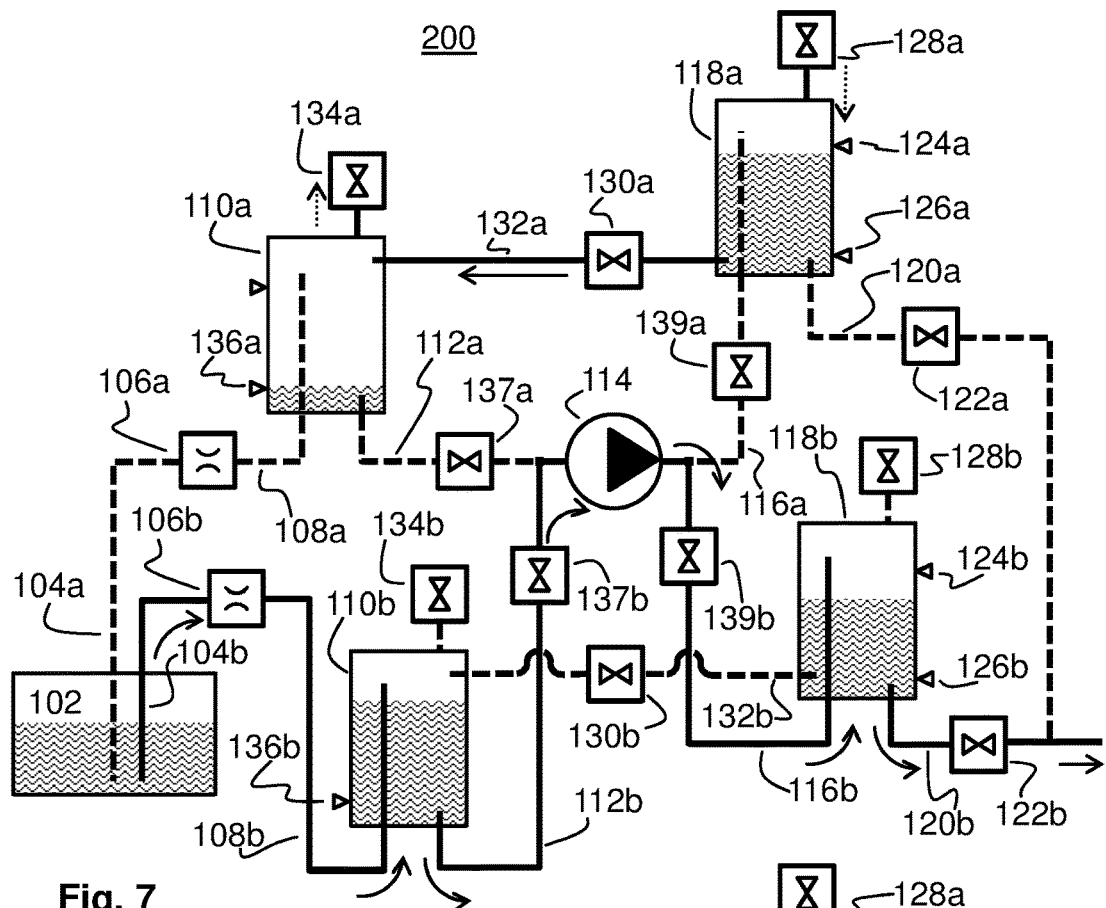

As soon as the level in the first chamber 110a has reached the level sensor 136a, the return starts in degassing system a by opening the return line 132a and degassing starts in degassing system b by opening the valves 137b, 139b, and 122b. This is shown in FIG. 7. The valve 122a is closed so that degassed liquid is only provided from the second chamber 118b.

Figure 8:
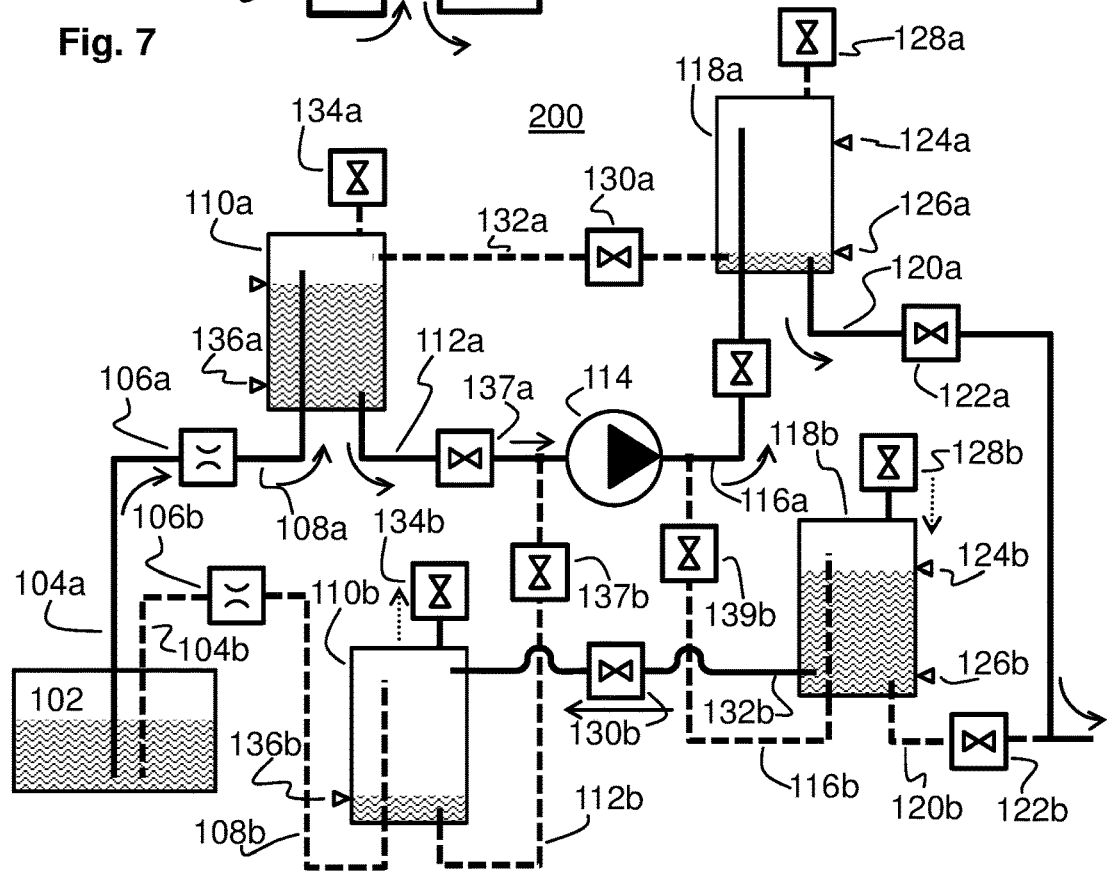

Once the liquid level in the first chamber 110b of degassing system b has reached the level sensor 136b, as is shown in FIG. 8, a switchover is made to the state shown in FIG. 8 in which the degassing takes place in degassing system a and a provision of degassed liquid takes place by opening the valve 122a and in which the return from the second chamber 118b into the first chamber 110b takes place in degassing system b with a closed valve 122b and an open valve 130b. The valves 137a and 139a are furthermore opened and the valves 137b and 139b closed.

Once the level in the first chamber 110a of degassing system a has reached the level sensor 136a, a switchover is again made to the state in accordance with FIG. 7.

Degassed liquid can always be provided at the outflow, i.e. at the removal unit downstream of the valves 122a/122b, due to the change of the operation of the degassing systems a, b arranged in parallel.

FIGS. 9 to 14 show a further embodiment of a degassing system 300 in accordance with the invention.

Figure 9:
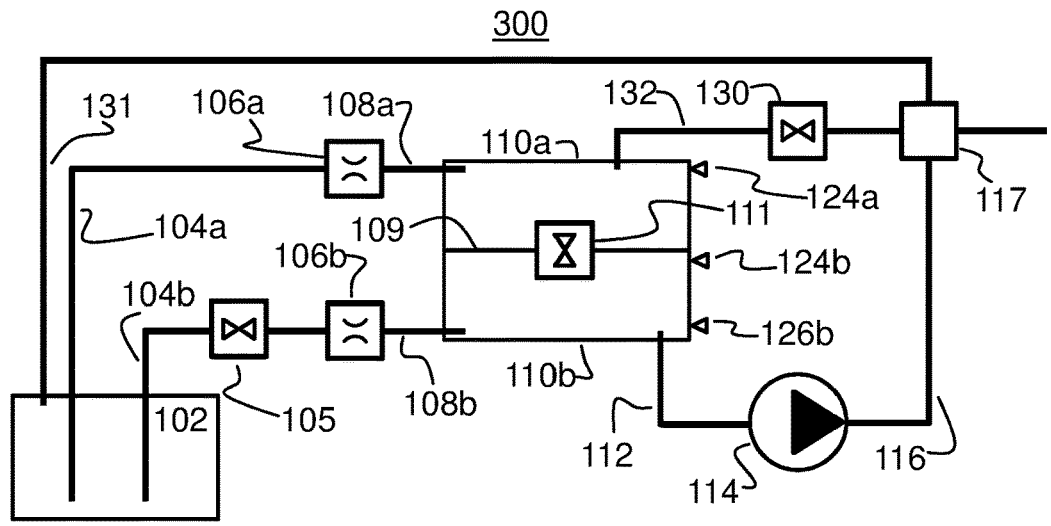

FIG. 9 shows the design of the system with a first degassing chamber 110a and with a second degassing chamber 110b that are separated from one another by a partition wall 109 in which a valve 111 is arranged. As can be seen from FIG. 9, the second chamber is located above the first chamber.

Both chambers 110a, 110b are connected to the storage container 102 via lines 104a, 104b, 108a, 108b in which a respective restrictor 106a, 106b is preferably arranged. A valve 105 is moreover arranged in the line leading to the second chamber 110b. The pump is connected to an intake line 112 that opens into the second chamber 110b and to a pressure line 116 that leads to a branch 117, i.e. to the removal unit. A connector facing to the right for a further use of the degassed liquid leads from this branch. This connector can, for example, be connected to an apparatus for preparing dialysis solution or to a dialysis machine.

A further line leads from the branch 117 back to the storage container (line 131) and a further line leads from the branch 117 back to the first chamber 110a (line 132 with valve 130).

Reference numeral 124a designates a level sensor in the first chamber 110a and reference numerals 124b and 126b designate level sensors in the second chamber 110b.

Figure 10:
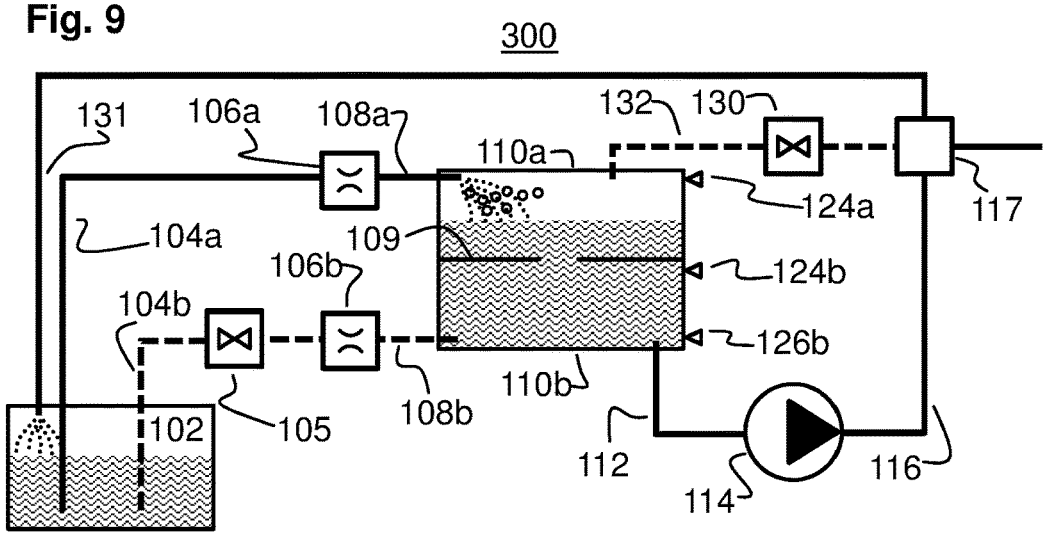

In the state in accordance with FIG. 10 (first phase of the degassing—first operating mode), the pump 114 conveys with a closed valve 105 via the line 104a and the restrictor 106a as well as the line 108a into the first degassing chamber 110a. The vacuum in the fluidically connected degassing chambers generated by the pump 114 serves this purpose. The gas shown by circles and liquid (dots) enter into the first degassing chamber 110a in a separated manner via the line 108a.

The pump conveys the degassed liquid from the second degassing chamber 110b to the branch 117. Some of the liquid is utilized for a use such as the preparation of a dialysis solution; a different portion of the liquid is conveyed back into the storage container 102 via the return line 131.

The return line 132 is cut off by means of the valve 130. The intake branch 104b, 108b to the second degassing chamber 110b is cut off by means of the valve 105.

Figure 11:
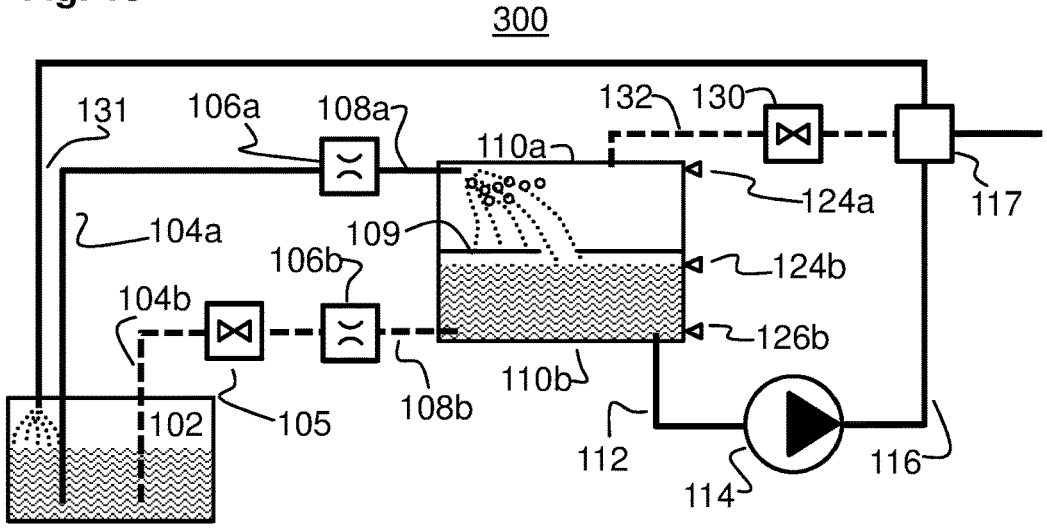

If the level in the degassing chambers connected by the open valve 111 drops below the level of the sensor 124b, as is shown in FIG. 11, the second phase of the degassing operation and thus also the return operation (second operating mode) is initiated.

Figure 12:
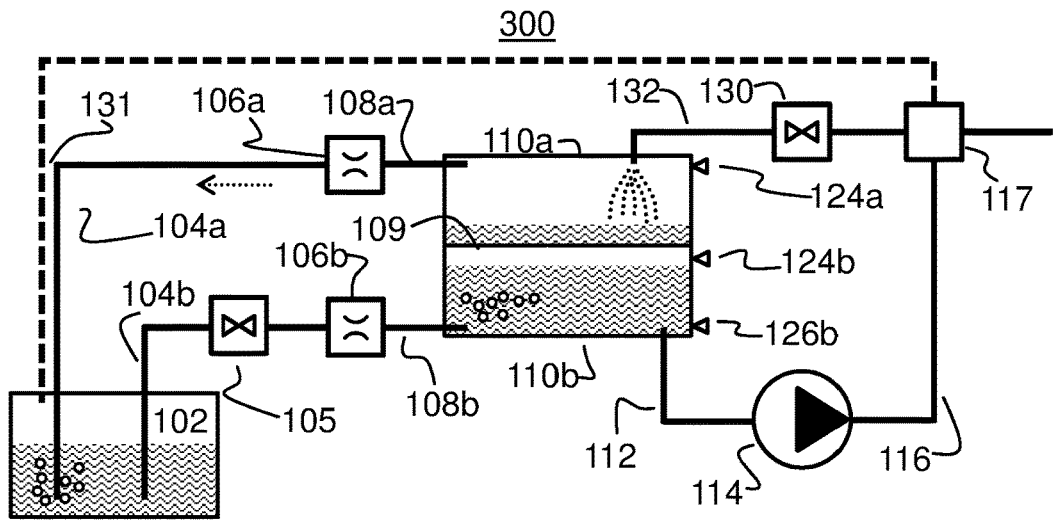

This second phase is reproduced in FIG. 12. The valve 11 is closed and thus fluidically separates the two degassing chambers from one another. The return line 132 is opened by opening the valve 130 and the intake branch 104b, 108b from the storage container 102 to the second degassing chamber 110b is opened by opening the valve 105.

The pump 114 conveys liquid from the second degassing chamber 110b and liquid is sucked from the storage container via the line 104b, 108b into the second degassing chamber 110b and is degassed. The second degassing chamber 110b is gradually emptied by the conveying of the pump 114 and the portion of the degassed liquid previously returned into the storage container via the return line 131 is now led back into the first degassing chamber 110a via the open return line 132. Displaced air escapes via the intake branch 104a and 108a in accordance with the dashed arrow and is shown in the form of bubbles in the storage container 102. Alternatively or additionally, a degassing valve, not shown, is used.

If the level sensor 124a of the first degassing chamber 110a fires because it is now correspondingly or largely filled, the second phase of the degassing operation ends. In the meantime, the second degassing chamber 110b is further emptied by the operation of the pump 114.

The firing of the level sensor 124a has the result that the valve 111 is opened again (cf. FIG. 14) so that the two degassing chambers are again connected to one another. Degassed liquid now flows from the first chamber 110a through the valve 111 into the second chamber 110b and fills it. The return line 132 is cut off by closing the valve 130 and a portion of the liquid not led off for a use flows via the line 131 back into the storage container 102. As in the state in accordance with FIG. 10, the intake branch 104b and 108b to the second chamber is cut off and the vacuum in the chambers connected to one another sucks fluid from the storage container 102 via the intake branch 104a and 108a into the first chamber 110a.

Figure 13:
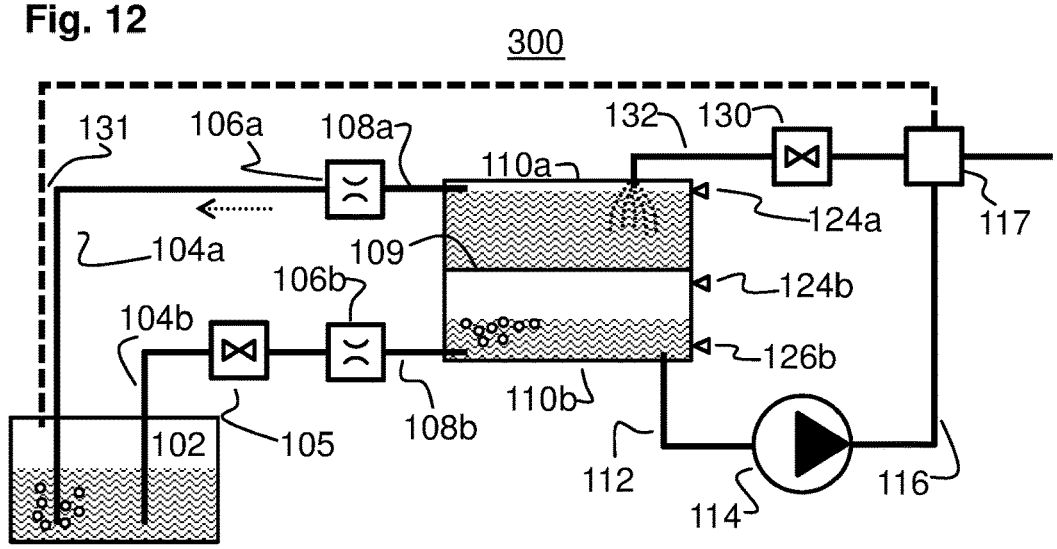
Figure 14:
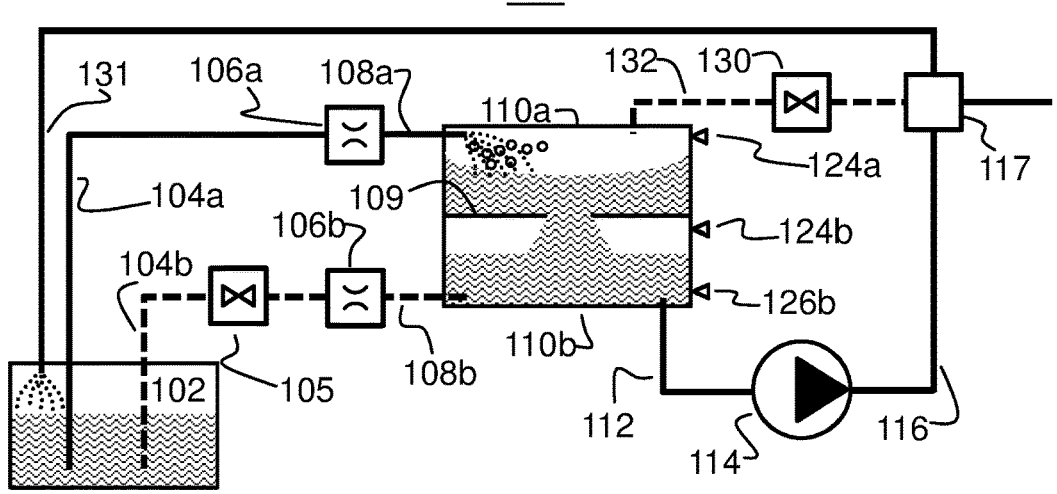

Degassed liquid is provided at the branch 117 both in the operating mode in accordance with FIG. 10 and in the operating mode in accordance with FIG. 13 so that a continuous operation or a semi-continuous operation is present.

The invention claimed is:

1. An apparatus for degassing liquids comprises a degassing system, wherein the degassing system has a first degassing chamber, a second degassing chamber, a liquid store, a pump, and a supply line that connects the liquid store to the first degassing chamber; wherein the pump is connected to the first degassing chamber at the intake side and to the second degassing chamber at the pressure side; and wherein the degassing system furthermore has a return line that can be cut off and that connects the two degassing chambers to one another, and wherein the apparatus comprises a controller that is configured to operate the degassing system in a first operating mode and in a second operation mode; wherein the degassing system is connected in the first operation mode such that the pump conducts liquid away from the first degassing chamber and supplies it to a removal unit for degassed liquid; and wherein the degassing system is connected in the second operating mode such that liquid is returned from the second degassing chamber to the first degassing chamber through the return line.

2. An apparatus in accordance with claim 1, characterized in that the pump is connected directly or indirectly to the first degassing chamber at the intake side and is connected directly or indirectly to the second degassing chamber or to the removal unit at the pressure side.

3. An apparatus in accordance with claim 1, characterized in that the controller is configured such that the pump is operated in a conveying mode in both operating modes; or in that the pump is only operated in a conveying mode in the first operating mode, but not in the second operating mode.

4. An apparatus in accordance with claim 1, characterized in that the first degassing chamber and the second degassing chamber are arranged relative to one another such that the liquid is conveyed through the return line from the second degassing chamber into the first degassing chamber due to gravity or due to the conveying power of the pump.

5. An apparatus in accordance with claim 1, characterized in that the two degassing chambers are spatially separated from one another or are arranged in a common construction unit that has a partition wall that separates the two degassing chambers from one another.

6. An apparatus in accordance with claim 1, characterized in that only the first degassing chamber is connected to the liquid store; or in that both degassing chambers are connected to the liquid store.

7. An apparatus in accordance with claim 1, characterized in that two degassing systems are provided that are connected in parallel; and in that the controller is configured such that the degassing systems are operated alternately such that the first degassing system is operated in the first operating mode and the second degassing system is simultaneously operated in the second operating mode and vice versa.

8. An apparatus in accordance with claim 1, characterized in that a level sensor for detecting the liquid level is present in the first degassing container and/or in the second degassing container; and in that the controller is configured to switch over from the first operating mode to the second operating mode or from the second operating mode to the first operating mode when a level sensor fires.

9. A method for degassing liquids by means of an apparatus in accordance with claim 1, wherein liquid is withdrawn from the first degassing chamber and is provided to a removal unit for degassed liquid in the first operating mode and wherein liquid is led back from the second degassing chamber into the first degassing chamber in the second operating mode.

10. A method in accordance with claim 9, characterized in that liquid is conveyed from the first degassing chamber via the second degassing chamber or to the exclusion of the second degassing chamber to the removal unit by means of the pump in the first operating mode.

11. A method in accordance with claim 9, characterized in that a switchover is made from the first operating mode to the second operating mode when the liquid level in the first degassing chamber falls below a limit value and/or exceeds a limit value in the second degassing chamber.

12. A method in accordance with claim 9, characterized in that a switchover is made from the second operating mode to the first operating mode when the liquid level in the second degassing chamber falls below a limit value and/or exceeds a limit value in the first degassing chamber.

13. A method in accordance with claim 9, characterized in that degassed liquid is only provided to the removal unit in the first operating mode or both in the first operating mode and in the second operating mode.

14. A method in accordance with claim 9, characterized in that both degassing chambers are arranged in a common construction unit that has a partition wall that separates the two degassing chambers from one another, wherein a valve or another cut-off element is provided in the partition wall that is open in the first operating mode and is closed in the second operating mode.

* * * * *